(12) United States Patent
Wendelstorf

(10) Patent No.: US 8,258,366 B2
(45) Date of Patent: Sep. 4, 2012

(54) DISPOSABLE HYGIENE ARTICLE

(75) Inventor: Carsten Wendelstorf, Koblenz (DE)

(73) Assignee: Paul Hartmann AG, Heidenheim (DE)

( * ) Notice: Subject to any disclaimer, the term of this patent is extended or adjusted under 35 U.S.C. 154(b) by 322 days.

(21) Appl. No.: 12/585,993

(22) Filed: Sep. 30, 2009

(65) Prior Publication Data

US 2010/0082005 A1    Apr. 1, 2010

Related U.S. Application Data

(63) Continuation of application No. 10/594,072, filed as application No. PCT/EP2005/003397 on Mar. 31, 2005, now abandoned.

(30) Foreign Application Priority Data

Apr. 3, 2004 (DE) .......................... 10 2004 016 552

(51) Int. Cl.
*A61F 13/15* (2006.01)
*A61F 13/20* (2006.01)

(52) U.S. Cl. ........................................ 604/358; 604/374

(58) Field of Classification Search .................. 604/374, 604/379, 385.28, 358
See application file for complete search history.

(56) References Cited

U.S. PATENT DOCUMENTS

| | | | |
|---|---|---|---|
| 4,642,110 A * | 2/1987 | Dudek ...................... | 604/385.21 |
| 4,685,915 A * | 8/1987 | Hasse et al. ................... | 604/378 |
| 5,422,169 A * | 6/1995 | Roe ............................... | 428/212 |
| 5,451,442 A | 9/1995 | Pieniak | |
| 5,514,104 A * | 5/1996 | Cole et al. ...................... | 604/366 |
| 5,868,724 A * | 2/1999 | Dierckes et al. ............... | 604/368 |
| 6,498,283 B1 | 12/2002 | Wada | |
| 6,575,952 B2 * | 6/2003 | Kirk et al. ....................... | 604/386 |
| 6,723,892 B1 * | 4/2004 | Daley et al. .................... | 604/378 |
| 6,764,477 B1 * | 7/2004 | Chen et al. ................. | 604/385.14 |
| 6,958,430 B1 * | 10/2005 | Marinelli ........................ | 604/375 |
| 7,825,291 B2 * | 11/2010 | Elfsberg et al. ................ | 604/378 |
| 2001/0021833 A1 * | 9/2001 | Schmidt et al. ........... | 604/385.01 |
| 2002/0177829 A1 * | 11/2002 | Fell et al. ................... | 604/385.01 |
| 2004/0033750 A1 * | 2/2004 | Everett et al. .................. | 442/381 |
| 2004/0054343 A1 * | 3/2004 | Barnett et al. ................. | 604/378 |
| 2004/0127870 A1 * | 7/2004 | DiPalma et al. ............... | 604/378 |
| 2005/0027267 A1 * | 2/2005 | Van Dyke et al. ............. | 604/367 |
| 2006/0282053 A1 * | 12/2006 | Rohrl ........................ | 604/385.01 |

FOREIGN PATENT DOCUMENTS

| | | |
|---|---|---|
| JP | 2189149 | 7/1990 |
| JP | 4200543 | 7/1992 |
| JP | 2000225138 | 8/2000 |
| JP | 2003070842 | 3/2003 |
| JP | 2004057416 | 2/2004 |

* cited by examiner

*Primary Examiner* — Tatyana Zalukaeva
*Assistant Examiner* — Susan Su
(74) *Attorney, Agent, or Firm* — Paul Vincent

(57) ABSTRACT

A disposable hygiene article has an absorbing element component (12) which is used for storing body liquids and can also contain superabsorbent materials. The absorbing element component (12) is provided with a first area (18, 20), an absorbent material of which has a mass per unit area that increases towards the lateral edges in the transversal direction (16) of the hygiene article. The storage capacity of a section (44) which extends along 40 to 90 percent of the length of the absorbing element component (12) in the longitudinal direction (14) is substantially constant relative to the longitudinal direction (14).

15 Claims, 8 Drawing Sheets

DISPOSABLE HYGIENE ARTICLE

This application is a continuation of Ser. No. 10/594,072 filed on Sep. 25, 2006 now abandoned as the national stage of PCT/EP2005/003397 filed on Mar. 31, 2005 and also claims Paris Convention priority of DE 10 2004 016 552.1 filed on Apr. 3, 2004, the entire disclosures of which are hereby incorporated by reference.

BACKGROUND OF THE INVENTION

The invention concerns a disposable hygiene article, comprising an absorbing element component which stores body liquids and may also contain superabsorbent materials.

A hygiene article with an absorbent material, the mass per unit area (basis weight) of which increases in an area in the transverse direction towards the side edges, is described in patent application DE 103 26 022.6 of the Assignee which was not previously published.

The crotch area of hygiene articles of the above-mentioned type, i.e. in particular baby diapers, incontinence diapers and pants, absorbent liners, as well as sanitary towels and panty liners, is problematic in that sufficient absorptive capacity must be provided, but the space between the legs of the user is limited. An excessive amount of voluminous absorbing element material in the crotch area is unpleasant for the user, and the material may twist and warp which impairs the function of the hygiene article. For this reason, it has been proposed to provide a maximum amount of superabsorbent, particulate materials in the crotch area, which have a high permanent storage capacity and a very small initial volume in the dry state, as is known per se and requires no further description. The above-mentioned document DE 103 26 022.6 also teaches displacement of the suction capacity from the crotch area towards the front and rear areas.

It is the underlying purpose of the present invention to provide a hygiene article having an optimum absorption capacity distribution, which is nevertheless comfortable for the user.

SUMMARY OF THE INVENTION

This object is achieved in a disposable hygiene article, with which the absorbing element component has a first area with an absorbent material mass per unit area (basis weight, for example, measured in grams per square meter) in this absorbing element component, which increases in the transverse direction of the hygiene article towards the side edges, wherein the storage capacity of a section extending in the longitudinal direction through 20 to 100% of the length of the absorbing element component is substantially constant in that longitudinal direction.

In accordance with the invention, an absorbing element component has an increasing mass per unit area and therefore an increasing storage capacity of an absorbent material in the transverse direction in at least one first area. The invention also proposes design of the absorbing element component in such a manner that it is optionally tapered in the crotch area (hour glass shape) and still has a substantially constant storage capacity in the longitudinal direction at least over a certain section length. In accordance with the invention, it has turned out that a rather uniform distribution of the storage capacity in the longitudinal direction of the hygiene article, especially for tapering absorbing element components, is accompanied by good comfort of wear, which again has a positive effect on the usage properties of the overall hygiene article, since the hygiene article and its absorbing element components are less deformed or displaced.

For further definition of the inventive idea, the section of constant storage capacity extends in the longitudinal direction over 30 to 90%, in particular 40 to 70%, and moreover, in particular 45 to 60%, of the length of the respective absorbing element component. This section will advantageously substantially be in the crotch area of the hygiene article, i.e. in the area between the legs of the user.

In a further particularly advantageous fashion, an absorbing element component has a second area with a mass per unit area of an absorbing material of this absorbing element component, which increases from the back and/or front area of the hygiene article towards the crotch area. This takes into account that, when viewing bordering longitudinal sections, tapered absorbing elements have a smaller surface due to the tapering, which would reduce the storage capacity in the tapered region for constant mass per unit area (from section to section). Since the mass per unit area of an absorbent material of the absorbing element component increases in the second area towards the crotch area which is, in particular, tapered, the storage capacity in the longitudinal direction can be kept substantially constant. When the storage capacities of absorbing element components in bordering longitudinal sections of a hygiene article or absorbing element of a length of 10 mm are compared, a deviation of up to ±15% is regarded as being substantially constant in accordance with the invention. The deviation is preferably less than 10%.

To state the inventive idea more precisely, the first area of increasing mass per unit area of an absorbent material of an absorbing element component increases in the transverse direction by 30 to 200%, in particular 30 to 150% and preferentially 50 to 120%.

The second area of increasing mass per unit area of an absorbent material of the absorbing element component increases in the longitudinal direction by 50 to 500%, in particular 50 to 400%, and preferentially by 100 to 350%.

In another advantageous fashion, the maximum mass per unit area of the second area of increasing mass per unit area is larger than the maximum mass per unit area of the first area of increasing mass per unit area. This also takes into account strong tapering in accordance with the invention.

The first area of increasing mass per unit area in the transverse direction must not necessarily be disposed in the crotch area of the hygiene article. Since the absorbing element or absorbing element component is intentionally tapered in the crotch area, this first area of increasing mass per unit area is advantageously separated from a center of the crotch area of the hygiene article. It may, in particular, be outside of the crotch area in a front area and/or a rear area of the hygiene article.

The crotch area is usually that area of a hygiene article which is disposed between the legs of a user during use. The center of the crotch area of a hygiene article can be determined by disposing an elastic thread or rubber band in the shape of an eight about the legs of a user standing upright or a baby lying on a flat support, such that the thread or band crosses at one point between the legs. This crossing point is defined as the center of the crotch area of the hygiene article during proper use. It is difficult to exactly define a natural delimitation between the crotch area and front area or rear area of the hygiene article. However, in order to obtain a quantitative delimitation, the crotch area is defined as that area of the hygiene article which extends from the center of the crotch area through 25% of the overall length of the absorbing element towards the front, and through 25% of the overall length of the absorbing element towards the rear of the hygiene article and merges into the front area and rear area, respectively at these locations.

In a further development of the latter inventive idea, two first areas of increasing mass per unit area are advantageously provided in a transverse direction and are separated from the center of the crotch area of the hygiene article in a longitudinal direction, i.e. in particular, in the front area or rear area of the hygiene article.

The first area or a line of maximum mass per unit area of the first area advantageously extends on both sides of the hygiene article over at least 15% of the length of the absorbing element component in the longitudinal direction. When viewing the absorbing element or absorbing element component from the top, strip-like first areas may in this case extend on both sides in the longitudinal direction. These strip-like areas may moreover preferably extend along side edge areas of the hygiene article, thereby forming a type of flank or flanking outlet protection.

In a particularly advantageous fashion, a first area of increasing mass per unit area extending in the transverse direction and a second area of increasing mass per unit area extending in the longitudinal direction directly abut or overlap each other. This is the case when the respective areas effectively merge due to the absorbing element topography.

As mentioned above, in a particularly advantageous variant of the invention, the width of the absorbing element component decreases from the rear and/or front area of the hygiene article towards the crotch area and the respective absorbing element component and, in particular, the overall absorbing element is tapered or has the shape of an hour glass or is T-shaped.

The increase in absorbent material of an absorbing element component as required in accordance with the invention can be realized in a particularly simple fashion through accumulation of the respective material. Corresponding shapes may thereby be used as negative molds, which then yield an absorbing element topography in correspondence with the increase in mass per unit area during production of the absorbing element or absorbing element component. Departing from such an absorbing element topography of substantially uniform density, the absorbing element or the respective absorbing element component may advantageously be subsequently compressed to a substantially uniform thickness after producing the topography. The areas of increasing mass per unit area also advantageously form areas of increasing density.

An inventive absorbing element component may comprise at least two absorbing element layers, wherein one of the absorbing element layers has a substantially uniform mass per unit area, i.e. has a constant uniform mass per unit area in the longitudinal and transverse directions. This layer may, in particular, be a basic or ground mat or a distributing layer facing the body.

The absorbing element component moreover advantageously has an absorbing element layer comprising cross-linked cellulose fibers. Cross-linked cellulose fibers swell elastically, in particular, in the wet state. They retain a large pore volume which is necessary for rapid absorption of liquid, and are not susceptible to "wet collapse". For this reason, they are suited for use as liquid-receiving and liquid-distributing layers of absorbent structures of hygiene articles which face the body.

In a further embodiment of the invention, the hygiene article advantageously comprises cuff elements which are upright at least in some areas, extend substantially in one longitudinal direction, are fixed at least along one cuff bottom line on the side of the article facing the body, and form lateral outlet barriers. "Cuff elements" are barrier or lateral outlet protection elements which are known per se and mostly comprise an elastifying component which causes the cuff elements to rise and abut against the surface of the user's skin during use.

These cuff elements moreover advantageously extend with varying (transverse) separations between the cuff bottom lines. In a further embodiment of this inventive idea, the first area of larger mass per unit area (in the transverse direction) has at least one partial area where the mutual separation between the cuff bottom lines is larger than outside of this partial area. In accordance with the invention, the cuff elements can be guided with varying separations between the cuff bottom lines, such that they have a larger separation from each other in a rear area, i.e. usually outside of a crotch area of the hygiene article, which produces a larger surface for receiving liquid. When, due to rapid liquid load, the liquid is distributed on the surface of the hygiene article, i.e. between the upright cuff elements, the receiving surface is advantageously as large as possible to ensure rapid liquid absorption. This means, however, that the cuff elements and the pockets formed thereby to receive body liquids, reach the vicinity of the absorbing element edge, where the absorption capacity is probably insufficient, or sufficient sealing or receiving capacity is not ensured due to the interaction with the edge of the absorbing element. The cuff elements are moreover connected to the materials of the hygiene article in such a manner that they disadvantageously enhance capillary liquid transport towards the edges of the hygiene article unless sufficient absorption capacity is provided at these locations. The present invention has shown that, by increasing the mass per unit area of an absorbent material of the absorbing element component at that location where the separation between the cuff bottom lines is larger than at another location, the liquid receiving characteristic of the hygiene article during use can be improved and its susceptibility to malfunction reduced.

The above-mentioned partial area is preferably disposed outside of a central longitudinal section of the hygiene article and at a separation from the center of the crotch area. It is shifted from the center of the crotch area towards the front area and/or the rear area.

The above-mentioned cuff elements are preferably guided in the longitudinal direction to have a maximum separation from each other. This maximum advantageously lies completely within the above-mentioned partial area of the first area of larger mass per unit area (in the transverse direction).

The maximum or the maxima of the separation between the cuff bottom lines is/are moreover advantageously located in a front area and/or rear area of the hygiene article.

The above-mentioned absorbing element component advantageously comprises a mixture of fibers and particulate superabsorbent materials.

Further features, advantages and details of the inventive hygiene article can be extracted from the enclosed claims, the drawing, and the following description of a preferred embodiment of the invention.

DESCRIPTION OF THE PREFERRED EMBODIMENT

Figure 1:
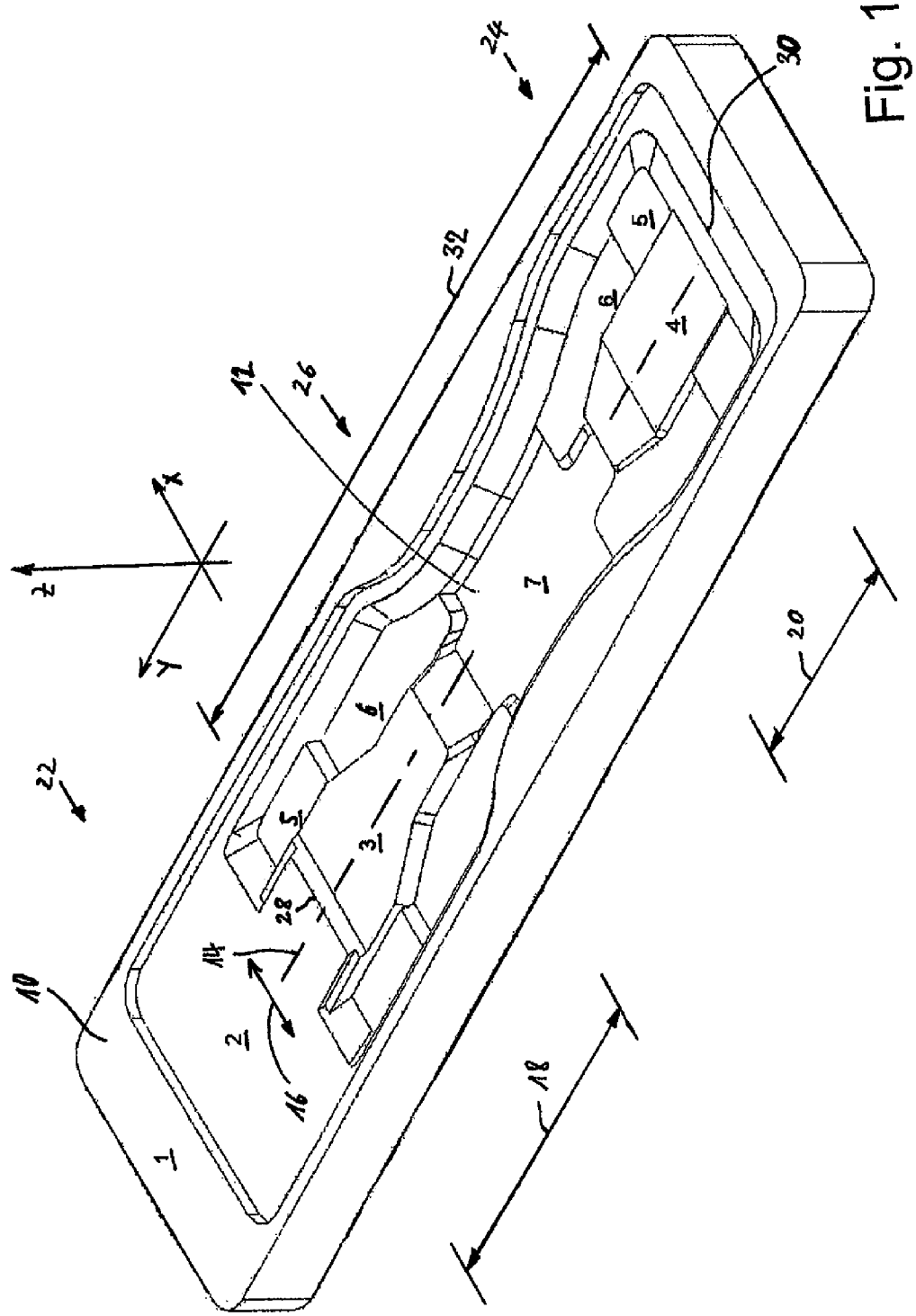
FIG. 1 shows a perspective view of a "negative" mold of an inventive absorbing element topography which can be formed by introducing or disposing the absorbing element materials into this "negative" mold with substantially uniform density.

An "absorbing element component" in accordance with the present invention means an entire absorbing element of a subject hygiene article, a layer of a multi-layer absorbing element, or a three-dimensional component thereof. "Storage capacity" in accordance with the present invention means the capacity for permanent storage of liquids within absorbing element materials, the capacity being determined and defined by the retention capacity in a centrifugal test, as is explained in detail below.

The above-mentioned section length of between 20 and 100% of the length of the observed absorbing element component is determined by a comparison of the storage capacity between longitudinal sections of the hygiene article, the absorbing element, or the absorbing element component. The absorbing element or absorbing element component is thereby disposed on a flat support and divided into longitudinal sections in the longitudinal direction, in particular, of a length of 5 to 40 mm and preferably into longitudinal sections of a length of approximately 20 mm. The storage capacity of each longitudinal section of the absorbing element or the absorbing element components is then experimentally determined and/or calculated for comparison purposes.

A centrifugal test is used to determine the storage capacity. The liquid retention of absorbent materials is thereby determined at a defined acceleration of 276 g (g=9.81 m/sec$^2$) after a centrifuging time of 4 min. This centrifugal test can be used to determine the storage capacity of any absorbent structures or any components of absorbent structures, such as fibers of a certain type, e.g. fluffed cellulose fibers, internally cross-linked cellulose fibers, or superabsorbent materials. Towards this end, the initial mass of a sample is determined using precision scales. The sample is then immersed for 20 min into a 99.5% NaCl solution (neither dyed nor denatured: in demineralized water).

The samples are then disposed against the drum wall of a centrifuge. If liquid-impermeable materials are present (such as backsheet foils), these are radially inwardly adjusted in order not to obstruct escaping liquid. The samples are then centrifuged at 276 g for 4 minutes and re-weighed. The liquid retention and therefore the storage capacity can be determined in grams as the difference between the determined masses subsequent to the centrifugal test ($M_{wet}$) and prior to the centrifugal test ($M_{dry}$):

Liquid retention=$M_{wet}$-$M_{dry}$(in g)

The result can also be expressed relative to the masses (in g/g) as:

$$\text{Liquid retention (relative)} = \frac{M_{wet} - M_{dry}}{M_{dry}}$$

The result is rounded to an integer number, and stated in g or g/g. The test number should be at least 6, wherein an average value x, $x_{min}$ and $x_{max}$ and preferably also the standard deviation S are determined.

In a particularly advantageous fashion, the storage capacity of the absorbent materials used for an absorbing element is determined in the above-mentioned fashion. The storage capacity of this absorbing element area can then be determined via the mass per unit area, i.e. considering or taking as a base the mass per unit area of a respective absorbent material in an absorbing element area. In this fashion, it is possible to state any storage capacity profile of an absorbing element or an absorbing element component for any region or direction.

Figure 1A:
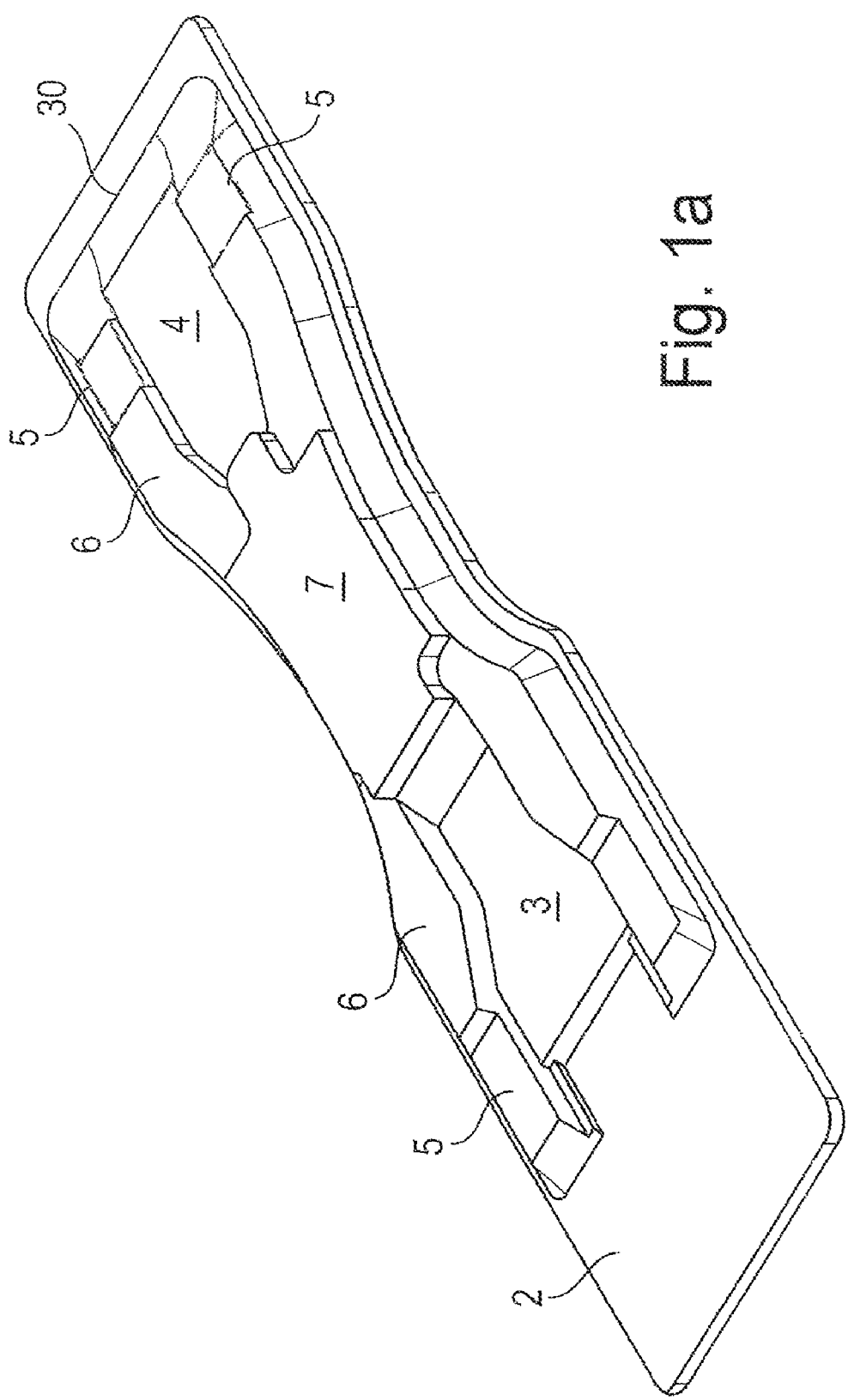
FIG. 1a shows a perspective view of the absorbing element produced by the mold if FIG. 1.

The substantially rectangular area of the mold designated with 1 in FIG. 1 designates the extension of a ground mat of fluffed cellulose fibers of a uniform mass per unit area. FIG. 1a shows the absorbing element produced by the mold of FIG. 1. Portions of FIG. 1a corresponding to the associated parts of FIG. 1 are labeled with the same reference symbols. The areas of the mold designated with reference numerals 2 through 7 form a three-dimensional volume, i.e. a topography, for the inventive design of an absorbing element component 12. The inventive absorbing element component 12 may e.g. be obtained by introducing a, per se, homogeneous mixture of fluffed cellulose fibers and superabsorbent particulate materials into the areas 2 through 7 of the mold. Depending on the depth of the mold in the Z-direction, the absorbing element component 12 has a more or less large mass per unit area of the absorbent material forming the absorbing element component 12.

Considering e.g. the areas 2 and 3, starting from a longitudinal center line 14 (extending in the longitudinal direction Y), and their transition to areas 5 and 6 (in the transverse direction 16), one can see that the mass per unit area of the absorbent material of the absorbing element component 12 in the transverse direction increases on both sides towards the side edges of the absorbing element component 12. This can be correspondingly observed starting from area 4 in the transverse direction 16 at the transition to areas 5, 6.

The absorbing element component 12 therefore has two first areas 18, with increasing mass per unit area of the absorbent material of this absorbing element component in the transverse direction 16 towards the side edges.

The mass per unit area of the absorbent material of the absorbing element component 12 also increases in the longitudinal direction 14 starting from a rear area 22 and a front area 24 towards a crotch area 26 intermediate between the first areas 18, 20. This increase in mass per unit area of the absorbing element component 12 starts at an edge 28, facing the crotch area 26, of the area 2 in the rear area 22 and at an edge 30 of the area 2 in the front area 24 without considering the ground mat 10. The area between the edges 28 and 30 is therefore called second area 32 of increasing mass per unit area of an absorbing material of the absorbing element component 12 in the longitudinal direction 14 towards the crotch area 26.

Figure 1B:
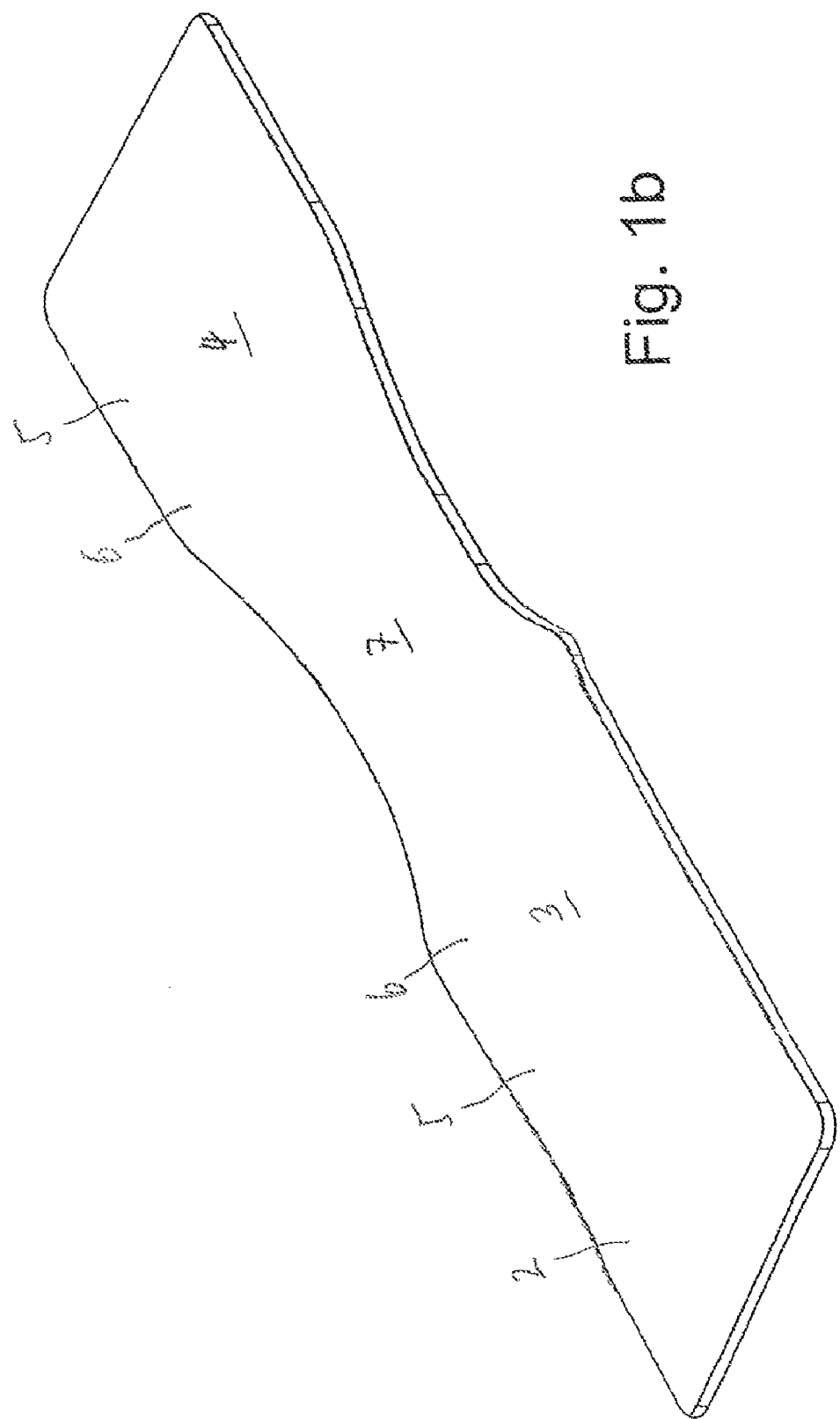
FIG. 1b shows a perspective view of an absorbing element component of substantially uniform thickness.

FIG. 1b shows an absorbing element component in accordance with the invention which has been compressed to a substantially uniform thickness so that areas of increasing mass per unit area also form areas of increasing density.

Figure 2:
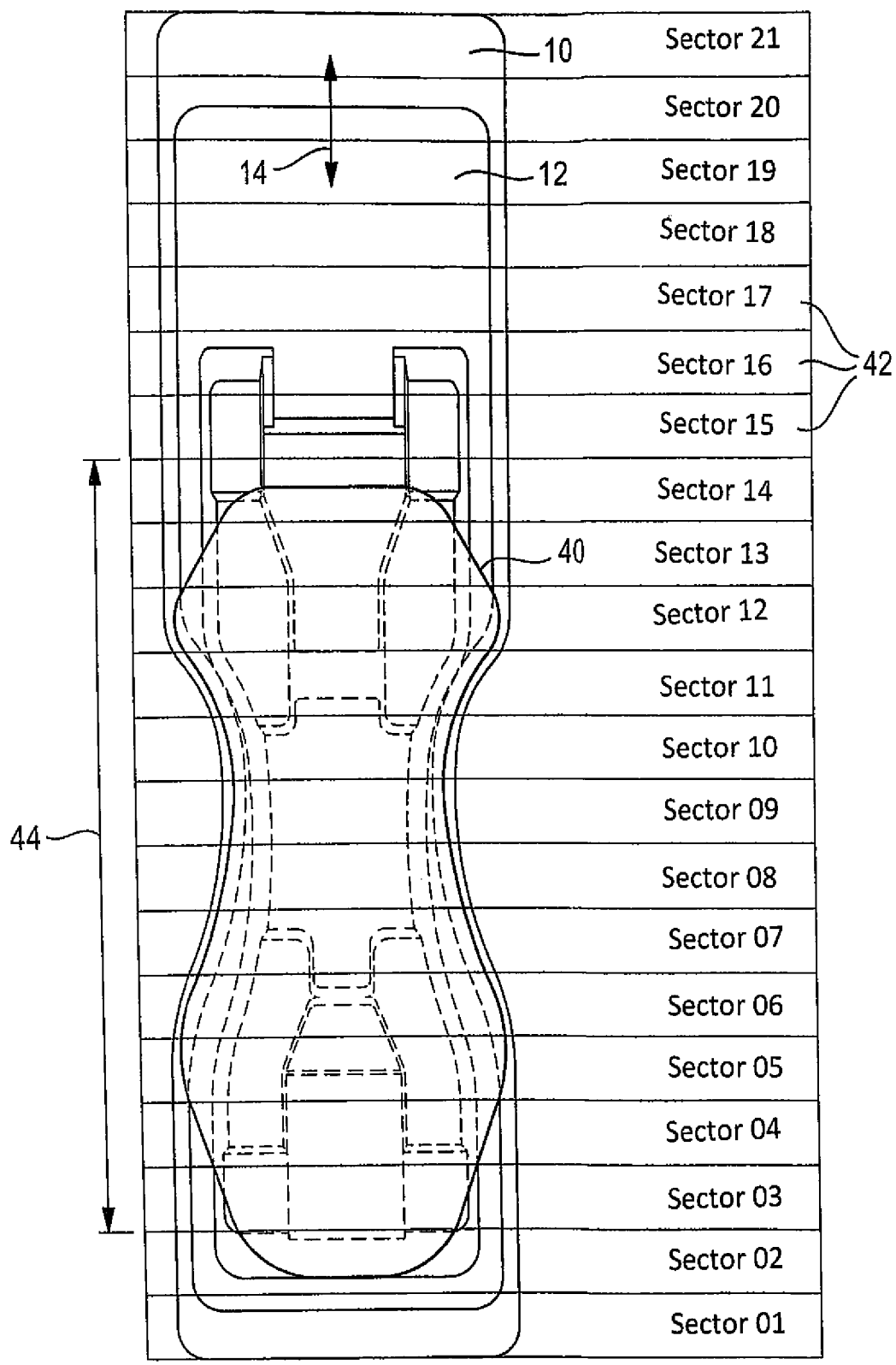
FIG. 2 shows a top view of an absorbing element which is formed using the "negative" mold of FIG. 1 together with a ground mat and a distributing layer.

FIG. 2 shows a top view of an absorbing element produced using the mold of FIG. 1 in a manner described in connection therewith, and the above-mentioned ground mat 10, the absorbing element component 12 and additionally a distributing layer 40 facing the body, which has an hour glass shape and covers approximately the parts of the three-dimensional structure of the absorbing element component 12, which corresponds to the areas 3 through 7. Portions disposed below upper lying structures are indicated with dashed lines. The illustrated absorbing element has a ground mat 10 having a uniform mass per unit area, an absorbing element component 12, shown herein as three-dimensional topology, and a distributing layer 40, also having a uniform mass per unit area. In the present case, which is only an example, the ground mat 10 consists of fluffed natural cellulose fibers, the absorbing element component 12 consists of a homogeneous mixture of natural fluffed cellulose fibers and superabsorbent particulate materials (SAP), and the distributing layer 40 consists of internally cross-linked cellulose fibers.

FIG. 2 shows a subdivision of the absorbing element into 21 longitudinal sections 42, i.e. sections of a length of approximately 20 mm abutting one another in the longitudinal direction 14.

The absorbing element component 12 is designed to have a substantially constant storage capacity in the longitudinal direction 14 over at least 20% of the length of the absorbing element component 12. The longitudinal sections 42 (sectors 01 to 21) are thereby used, whose storage capacity is determined as mentioned above.

The following table shows the mass per unit areas of an exemplary and preferred absorbing element composition in each area 1 through 7 of the topology of FIG. 1. It shows the mass per unit areas of natural fluffed cellulose fibers ("fluff") or internally cross-linked cellulose fibers of the distributing layer 40 ("CF") and the mass per unit areas of superaborbent particle materials ("SAP"), each in g/m².

| G/m² | Fluff | CF | SAP |
| --- | --- | --- | --- |
| Level 1 | 136 | 0 | 0 |
| Level 2 | 289 | 0 | 211 |
| Level 3 | 367 | 215 | 327 |
| Level 4 | 382 | 215 | 340 |
| Level 5 | 395 | 0 | 352 |
| Level 6 | 444 | 215 | 425 |
| Level 7 | 708 | 215 | 789 |

The applicant has determined the retention value of the used superabsorbent materials, the internally cross-linked cellulose fibers ("CF"), and the natural fluffed cellulose fibers ("fluff"). The retention value for fluffed natural cellulose fibers and internally cross-linked cellulose fibers was 1 g/g and for the superabsorbent materials 30 g/g in accordance with the above-mentioned method. From these values, we can calculate the storage capacity available in any longitudinal section 42 (sectors 1 through 21) thereby taking into consideration the area or volume portions of the respective areas 1 through 7. The result is shown in FIGS. 3 and 4.

Figure 3:
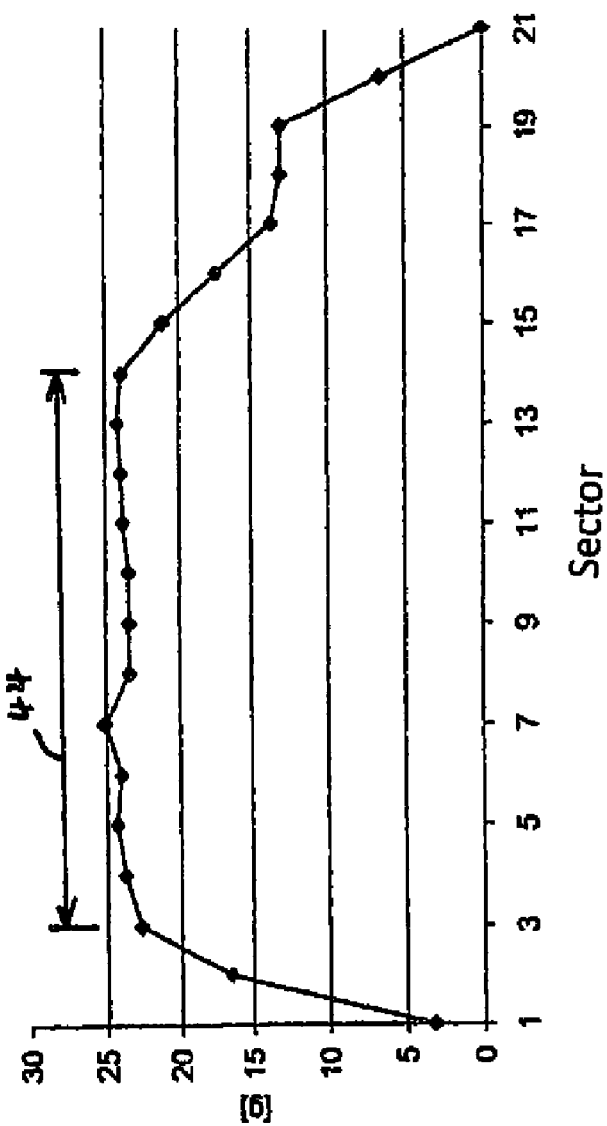
FIG. 3 shows the storage capacity of the absorbing element in longitudinal sections.
Figure 4:
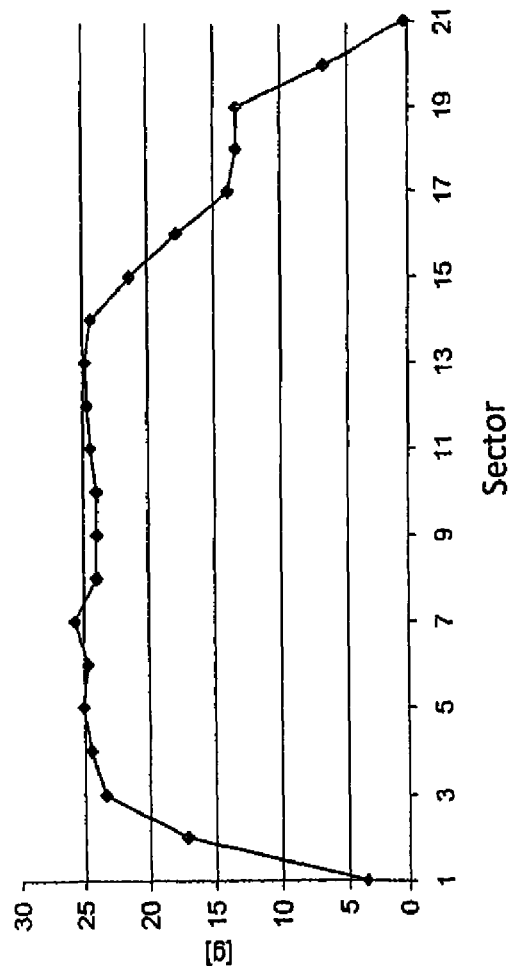
FIG. 4 shows the storage capacity of the absorbing element in longitudinal sections with the ground mat and distributing layer.

FIGS. 3 and 4 show the storage capacity (in g of the storable liquid) in the form of a table and diagram. The ground mat 10 and the distributing layer 40 were taken into consideration in the values which are slightly higher in FIG. 4 and the associated table.

The storage capacity in a section 44 of the absorbing element component which comprises sectors 3 through 14 of the longitudinal sections 42, is substantially constant over the longitudinal sections 42, i.e. in the longitudinal direction 14.

Figure 5:
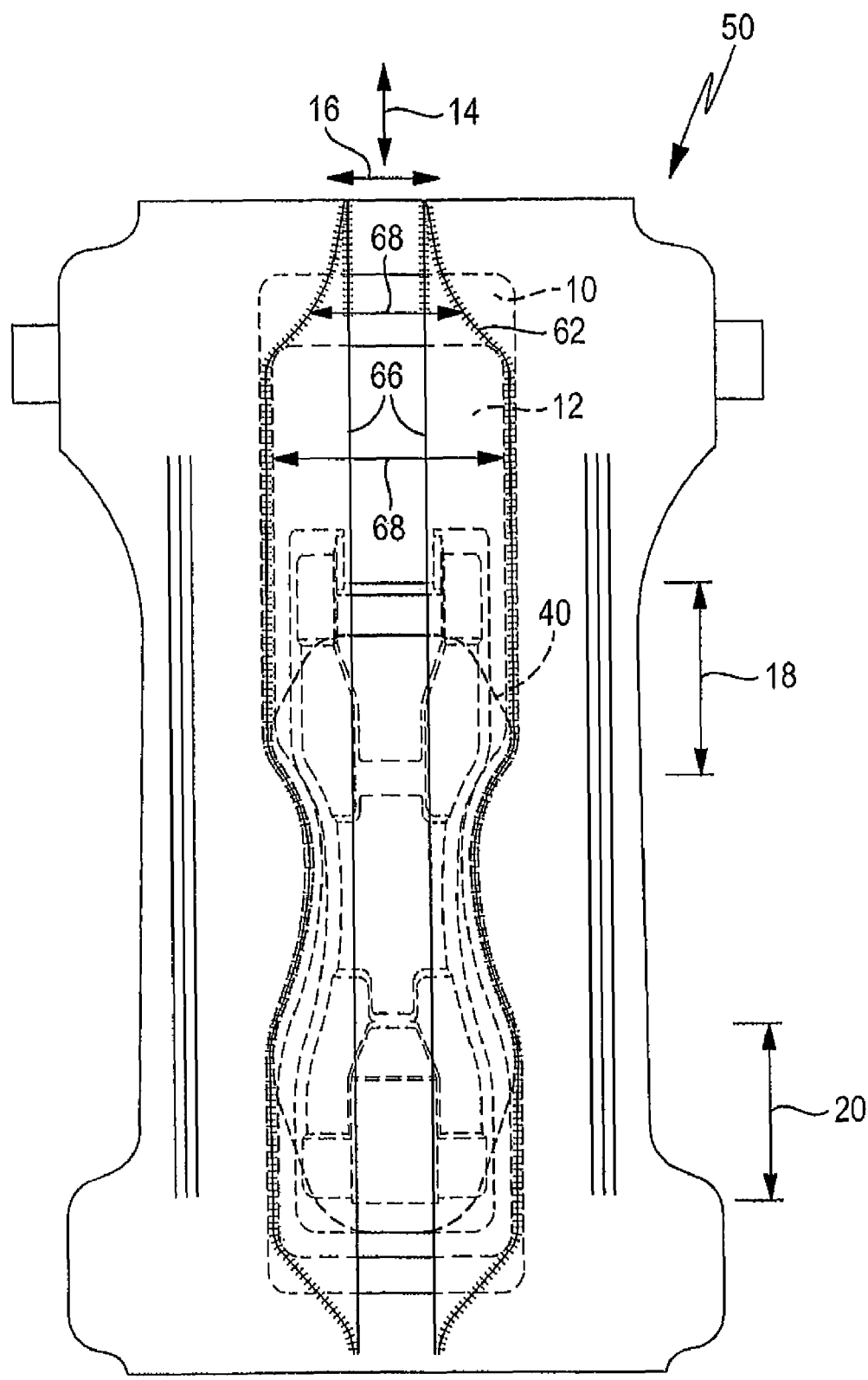
FIG. 5 (schematically) shows a top view of an inventive hygiene article.
Figure 6:
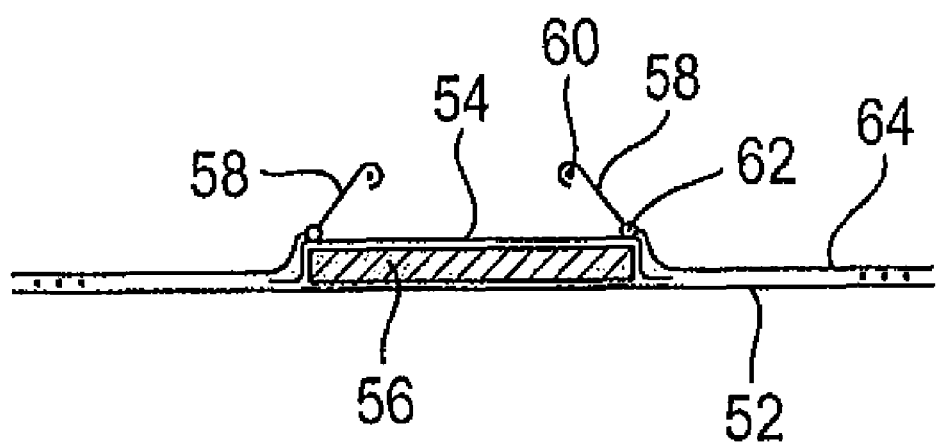
FIG. 6 shows a schematic view of a section through the hygiene article in accordance with the invention.

FIG. 5 finally shows a schematic top view and FIG. 6 shows a schematic sectional view of an inventive hygiene article 50 in the form of a diaper. Portions disposed below upper lying structures are indicated with dashed lines. The hygiene article 50 comprises a liquid-impermeable backsheet 52 facing away from the body, and a liquid-permeable topsheet 54 with an intermediate absorbing element 56, which comprises the above-described ground mat 10, absorbing element component 12 and distributing layer 40. The schematic view of FIG. 6 shows the topography of the absorbing element component 12 in accordance with the invention. It also shows lateral liquid barriers, so-called upright cuff elements 58 with elastification elements 60 at the distal end. These conventional cuff elements 58 are connected to the chassis materials, usually to a non-woven component of the topsheet 54 and/or to a further cover layer component 64 along a cuff bottom line 62. The reference numeral 66 in FIG. 5 indicates the distal end of the cuff elements 58. The illustration of FIG. 5 shows a varying separation 68 between the cuff bottom lines 62, i.e. in the transverse direction 16 of the hygiene article 50 along the longitudinal direction 14. The separation between the cuff bottom lines in the longitudinal direction of the hygiene article passes through two maxima, and the maxima overlap the respective first area 18, 20 of increasing mass per unit area of an absorbent component in the transverse direction 16. A high absorption capacity in the absorbing element edge region is thereby ensured in regions of maximum separation 68 between the cuff bottom lines 62. These first regions 18, 20 of increasing mass per unit area in the transverse direction extend approximately like strips in the side edge regions of the absorbing element 56. They form approximately the legs of the letter "H" or "X", as viewed from the top, wherein in the present case, the mass per unit area of the absorbent material does not increase in the transverse direction of the hygiene article in the crotch area or at least in the area bordering the center of the crotch area.

The schematic section of FIG. 6 shows a substantially flat absorbing element 56. Such an element can be formed by compressing the absorbing element of FIG. 1a to a substantially uniform thickness. In so doing, areas of increased mass per unit area form areas of increased density.

I claim:

1. A disposable hygiene article having an absorbing element component for storing body liquids, the absorbing element component comprising:

a respective front and rear first area being respectively separated from a center of a crotch area of the hygiene article and having a mass per unit area of absorbent material that increases starting from a longitudinal center line extending in a longitudinal direction of the hygiene article in a transverse direction towards side edges of the hygiene article so that a mass per unit area of the absorbent material of the absorbing element component increases in said transverse direction on both sides of said longitudinal center line towards side edges of the absorbing element component, the absorbing element component further comprising a respective front and rear second area having a mass per unit area of absorbent material which increases in said longitudinal direction from front and rear respectively of the hygiene article towards the crotch area thereof and is maximum within said crotch area, wherein the absorbing element component has a width which decreases from front and rear respectively of the hygiene article towards said crotch area, wherein a storage capacity of a section extending in a longitudinal direction over at least 40% to a maximum of 90% of a length of the absorbing element component is substantially constant along said longitudinal direction, wherein said mass per unit area of absorbent material in said respective front and rear first area increases in said transverse direction by 30 to 200%.

2. The hygiene article of claim 1, wherein said section of constant storage capacity extends over 40 to 70% of the length of the absorbing element component.

3. The hygiene article of claim 1, wherein said mass per unit area of absorbent material in said respective front and rear second area increases in said longitudinal direction by 50 to 500%.

4. The hygiene article of claim 1, wherein a maximum mass per unit area of said respective front and rear second area of increasing mass per unit area is larger than a maximum mass per unit area of said respective front and rear first area of increasing mass per unit area.

5. The hygiene article of claim 1, wherein a line of maximum mass per unit area of said respective front and rear first area extends in said longitudinal direction on both sides of the hygiene article over at least 15% of a length and along side edge areas of the absorbing element component.

6. The hygiene article of claim 1, wherein said respective front and rear first area of increasing mass per unit area in said transverse direction and said respective front and rear second area of increasing mass per unit area in said longitudinal direction are disposed in direct abutment to or overlapping with each other.

7. The hygiene article of claim 1, wherein the absorbing element component is compressed to a substantially uniform thickness so that areas of increasing mass per unit area also form areas of increasing density.

8. The hygiene article of claim 1, wherein the absorbing element component comprises at least two absorbing element layers.

9. The hygiene article of claim 8, wherein an absorbing element layer has a substantially uniform mass per unit area.

10. The hygiene article of claim 1, wherein the absorbing element component has an absorbing element layer comprising cross-linked cellulose fibers.

11. The hygiene article of claim 1, wherein the hygiene article further comprises cuff elements extending substantially in a longitudinal direction and elevated at least in certain areas, said cuff elements forming lateral outlet barriers and being fixed at least along a cuff bottom line on a side of the article facing a user's body.

12. The hygiene article of claim 11, wherein said cuff elements include varying separation distances between cuff bottom lines.

13. The hygiene article of claim 11, wherein said respective front and rear first area of larger mass per unit area comprises at least one partial area in which a mutual separation distance between said cuff bottom lines is larger than outside of said partial area.

14. The hygiene article of claim 13, wherein a maximum separation distance between said cuff bottom lines is disposed in a front area and a rear area of the hygiene article.

15. The hygiene article of claim 1, wherein the absorbing element component comprises a mixture of fibers and particulate superabsorbent materials.

* * * * *